US005227366A

United States Patent [19]

Swatling et al.

[11] Patent Number: 5,227,366
[45] Date of Patent: Jul. 13, 1993

[54] MITIGATION OF STRESS-CRACKING IN FRAGRANCED BLEACH-CONTAINING BOTTLES

[75] Inventors: Donald K. Swatling, El Cerrito; Peter C. Arbogast, Sunol, of Calif.

[73] Assignee: The Clorox Company, Oakland, Calif.

[21] Appl. No.: 815,453

[22] Filed: Dec. 31, 1991

Related U.S. Application Data

[62] Division of Ser. No. 384,338, Jul. 24, 1989, Pat. No. 5,080,826, which is a division of Ser. No. 83,753, Aug. 7, 1987, Pat. No. 4,863,633.

[51] Int. Cl.[5] .......... A61K 7/46
[52] U.S. Cl. .......... 512/2; 512/1; 252/174.11
[58] Field of Search .......... 512/2; 252/174.11

[56] References Cited

U.S. PATENT DOCUMENTS

| | | | |
|---|---|---|---|
| 2,834,737 | 5/1958 | Farkas | 252/187 |
| 3,214,052 | 10/1965 | Dike | 215/10 |
| 3,331,503 | 7/1967 | Brown | 206/65 |
| 3,348,567 | 10/1967 | Beeby | 206/45.33 |
| 3,369,688 | 2/1968 | Dike | 215/10 |
| 3,387,749 | 6/1968 | Godshalk | 222/143 |
| 3,391,824 | 7/1968 | Wiseman | 220/97 |
| 3,474,843 | 10/1969 | Maris | 150/3.5 |
| 3,560,389 | 2/1971 | Hunting | 252/95 |
| 3,583,590 | 6/1971 | Ferraro | 215/10 |
| 3,587,910 | 6/1971 | McCarthy | 220/23.4 |
| 3,680,735 | 8/1972 | Lucas | 220/97 R |
| 3,684,722 | 8/1972 | Hynam et al. | 252/98 |
| 3,757,983 | 9/1973 | McCarthy | 220/23.4 |
| 3,860,525 | 1/1975 | Bechtold | 252/99 |

(List continue on next page.)

FOREIGN PATENT DOCUMENTS

| | | | |
|---|---|---|---|
| 206718 | 12/1986 | European Pat. Off. . | |
| 3527910 | 2/1987 | Fed. Rep. of Germany . | |
| 138635 | 4/1985 | France | 512/2 |
| 5015438 | 2/1980 | Japan | 512/2 |
| 60-179465 | 9/1985 | Japan . | |
| 60-179500 | 9/1985 | Japan . | |
| 60-205200 | 9/1987 | Japan . | |
| 62-250200 | 9/1987 | Japan . | |
| 3189154 | 8/1988 | Japan | 512/2 |

OTHER PUBLICATIONS

Zisman, "Relationship of the Equilibrium Contact Angle to Liquid and Solid Constitution," *Adv. in Chem.*, Ser. 43 (1964).
Rath, "The Nature of Hydrotropy and Its Significance for the Chemical Technology," Tenside, vol. 2, pp. 1–6 (1965).
Saleh et al., "Hydrotropic Agents: A New Definition," Int. J. of Pharmaceutics, vol. 24, pp. 231–238 (1985).
Neuberg, "Hydrotropic Phenomena," Biochem. Zeitschrift, vol. 79 pp. 107–176 (1916).
Lawrence et al, "Solubilization and Hydrotropy,"

(List continued on next page.)

*Primary Examiner*—Richard D. Lovering
*Assistant Examiner*—Joseph D. Anthony
*Attorney, Agent, or Firm*—Joel J. Hayashida; Michael J. Mazza; Harry A. Pacini

[57] ABSTRACT

This invention relates to a storage and shipping system comprising corrugated containers which house plastic vessels or bottles used to hold fragranced liquid bleaches in which the shipping and storage containers are stacked on top of one another. In the stacks, in all of the shipping and storage containers except for the topmost one, the plastic vessels will share some of the vertical component of the compression load caused by the shipping and storage container directly located above a given shipping and storage container. In a further embodiment of the invention, the problem of surface wetting of blown polyethylene bottles by certain additives in liquid bleach is recognized and addressed. In another embodiment of the invention is provided a stable fragranced bleaching composition. In a still further embodiment of this invention is provided a homogeneous fragrance preblend and a method of making thereof.

5 Claims, 2 Drawing Sheets

U.S. PATENT DOCUMENTS

| | | | |
|---|---|---|---|
| 3,876,551 | 4/1975 | Laufer et al. | 252/98 |
| 3,933,268 | 1/1976 | Buske | 220/23.4 |
| 4,061,247 | 12/1977 | Meshberg | 222/1 |
| 4,113,645 | 9/1978 | De Simone | 252/187 H |
| 4,127,207 | 11/1978 | Hubert et al. | 215/1 C |
| 4,154,694 | 5/1979 | Donaldson | 252/98 |
| 4,172,539 | 10/1979 | Botkin | 222/195 |
| 4,276,987 | 7/1981 | Michel | 215/1 C |
| 4,282,109 | 8/1981 | Citrone et al. | 252/102 |
| 4,287,084 | 9/1981 | Boden et al. | 252/187 H |
| 4,303,555 | 12/1981 | Boden et al. | 252/522 R |
| 4,308,179 | 12/1981 | Celli | 512/2 |
| 4,308,955 | 1/1982 | Schieser et al. | 206/509 |
| 4,337,163 | 6/1982 | Schilp | 252/96 |
| 4,339,344 | 7/1982 | Boden et al. | 252/187.24 |
| 4,342,663 | 8/1982 | Boden et al. | 252/186.36 |
| 4,347,153 | 8/1982 | Hooper et al. | 252/174.25 |
| 4,388,204 | 6/1983 | Dimond et al. | 252/98 |
| 4,390,448 | 6/1983 | Boden et al. | 252/187.26 |
| 4,399,050 | 8/1983 | Bentham et al. | 252/95 |
| 4,541,529 | 9/1985 | Hestehave et al. | 206/510 |
| 4,541,951 | 9/1985 | Hall et al. | 252/522 R |
| 4,576,728 | 3/1986 | Stoddart | 252/102 |
| 4,579,677 | 4/1986 | Hooper et al. | 252/95 |
| 4,599,186 | 7/1986 | Choy et al. | 252/102 |
| 4,623,476 | 11/1986 | Nayar et al. | 252/94 |
| 4,657,692 | 4/1987 | Choy et al. | 252/99 |
| 4,708,816 | 11/1987 | Chang et al. | 252/186.25 |
| 4,863,633 | 9/1989 | Colborn et al. | 252/187.26 |
| 5,080,826 | 1/1992 | Colborn et al. | 252/187.25 |

Chemistry, Physics and Application of Surface Active Substances, vol. II, pp. 673–708 (1965).

R. Cramer, U.S. Ser. No. 07/220,977, filed Jul. 18, 1988, "Bleaching and Brigtening Composition and Method" (Cont. of Ser. No. 07/096,749, filed Sep. 16, 1987 and Ser. No. 748,3056 filed Jun. 24, 1985, both now abandoned).

R. Cramer, et al., U.S. Ser. No. 07/220,979, filed Jul. 18, 1989, "Bleaching and Bluing Composition and Method" (Cont. of Ser. No. 07/089,927, filed Aug. 25, 1987, Ser. No. 840,974, filed Mar. 13, 1986, and Ser. No. 74,565 filed Jan. 27, 1984, all of which have been abandoned).

"Tilex®"]Mildew Stain Remover, U.S. Trademark Reg. 1,220,499, sold by Clorox nationally at least as early as 1981.

B. Haendler, U.S. Ser. No. 921,236, filed Oct. 20, 1986, "Stable Emulsified Bleaching Compositions".

R. Cramer et al., U.S. Ser. No. 07/173,000, filed Mar. 23, 1988, "Thickened Hypochlorite Composition," (CiP of Ser. No. 894,234, filed Aug. 7, 1986, now abandoned).

Kirk-Othmer, Encyclopedia of Chemical Technology, 3rd Ed., vol. 3, "Barrier Polymers," pp. 480–502 (1978).

Kirk-Othmer, Encyclopedia of Chemical Technology, 3rd Ed., vol. 9, "Engineering Plastics," pp. 118–137 (1981).

Kirk-Othmer, Encyclopedia of Chemical Technology, 3rd Ed., vol. 16, "Olefin Polymers," pp. 385–499 (1981).

Kirk-Othmer, Encyclopedia of Chemical Technology, 3rd Ed., vol. 18, "Plastics Processing," pp. 184–206 (1982).

MITIGATION OF STRESS-CRACKING IN FRAGRANCED BLEACH-CONTAINING BOTTLES

This is a division, of application Ser. No. 07/384,338, filed Jul. 24, 1989 now U.S. Pat. No. 5,080,826, itself a division, of application Ser. No. 07/083,753, now U.S. Pat. No. 5,080,826 filed Aug. 7, 1987, now U.S. Pat. No. 4,863,633.

BACKGROUND OF THE INVENTION

1. Field of the Invention

This invention relates to a storage and shipping system comprising corrugated containers which house plastic vessels or bottles used to hold fragranced liquid bleaches in which the shipping and storage containers are stacked on top of one another. In the stacks, in all of the shipping and storage containers except for the topmost one, the plastic vessels will share some of the vertical component of the compression load caused by the shipping and storage container directly located above a given shipping and storage container. In a further embodiment of the invention, the problem of surface wetting of blown polyethylene bottles by certain additives in liquid bleach is recognized and addressed. In another embodiment of the invention is provided a stable fragranced bleaching composition. In a still further embodiment of this invention is provided a homogenous fragrance preblend and a method of making thereof.

2. Brief Description of the Prior Art

Liquid bleaches, both hypochlorite and hydrogen peroxide based products, have found wide commercial acceptance and are commonly used in a variety of household cleaning and laundering products. However, in the quest to provide more diverse products to consumers, it is desirable to add certain esthetic adjunct materials to these liquid bleaches. Fragrances, for instance, have been added to liquid hypochlorite bleaches to impart a pleasing scent. As with other liquid bleach products, such fragranced bleaches would be packaged in plastic, relatively thin-walled bottles or jugs. These plastic bottles or jugs are typically shipped in shipping and storage containers made of corrugated material.

Beeby, U.S. Pat. No. 3,348,667 disclosed a combination shipping and display container in which vertical partitions are used to absorb the compression load due to other containers, and expressly provides that articles, such as cylindrical containers, contained therein, do not bear any portion of such compression load. Dike, in his U.S. Pat. No. 3,214,052 and U.S. Pat. No. 3,369,688, provides plastic bottles used to house hypochlorite bleaches or the like which have an interlocking base and handle configuration in which the base of the bottle is indented to allow for nesting and interlocking of the handle of the bottle directly below it. Godshalk et al, U.S. Pat. No. 3,387,749 discloses a plastic container having a recessed base such that the side portions of the base rest upon on reinforced sections directly below it. Yet one other reference, Hubert et al, U.S. Pat. No. 4,127,207 shows that plastic containers can have interlocking bottle shoulder and base arrangements.

In order to distribute the load evenly so that no damage is caused to the plurality of plastic vessels or bottles, because of compression load stress caused by stacking the containers, virtually no headspace is provided between the tops of the plastic bottles (which typically includes the closure) and the top wall or panel of the carton. In this manner, each of the plastic vessels or bottles share some of the vertical component of the compression load bearing on the carton, usually from another similarly filled carton. It is important to loadshare in this manner, since crushed or damaged cartons present not merely esthetic or appearance problems; even weight distribution prevents or alleviates the problem of stressing the plastic bottles beyond their "safe" load bearing capacity. Additionally, crushed containers, such as those on the bottom of the stack, can actually collapse, causing the entire stack to topple. However, the need to loadshare in order to prevent damage to the containers and contents must be balanced by the need to prevent too great compression on the plastic bottles, which, because of their relatively thin-walled construction, can be damaged by too great a vertical load.

It is further surprising and heretofore unknown that there is a relationship between the type of dispersing material used to disperse immiscible adjuncts such perfumes or fragrances throughout a substantially aqueous liquid bleach composition housed in such plastic bottles or vessels and the amount of stress-cracking which occurs in such plastic vessels or bottles, especially when a compression load is placed thereon.

SUMMARY OF THE INVENTION

The invention relates to a storage and shipping system comprising a plurality of shipping containers, each of which containers bears a compression load from at least one other container borne atop the initial container (except for the uppermost container), in which each of said containers houses a plurality of plastic, relatively thin-walled vessels, said vessels containing a fragranced liquid bleach composition, said vessels sharing at least a portion of the vertical component of said compression load; wherein said liquid bleach composition comprises:

(a) an aqueous liquid bleach;

(b) adjuvants or mixtures thereof which are immiscible, insoluble or only partially soluble in said liquid bleach, e.g., solvents, fragrances, FWA, dyes, pigments, opacifying agents, etc.; and (c) agents for dispersing said adjuvants in said liquid bleach so that a substantially one phase composition results.

The dispersing agents may include one or more of, a hydrotrope, polymeric dispersing agent, or a low concentration of surfactant, or a combination of any of the foregoing, such that the agent at its use concentration does not lower the surface tension of the aqueous content below the critical surface tension of the plastic bottle. Critical surface tension is hereinafter defined.

The present invention overcomes the disadvantages that occur when a corrugated carton bearing plastic bottles containing liquid bleaches which have been fragranced (or contain some other immiscible adjunct) and which have had the fragrance dispersed by surfactants or the like. The use of surfactants and other materials which appear to form micelles in aqueous media, appears to increase decomposition of the plastic in the bottles by "wetting" or increasing the susceptibility of the surface area of the interior of the plastic bottle to attack by oxidation, increased absorption of solvents and surfactants which weaken the structure, or by other means which are not presently fully understood. Because the plastic bottles will take up some of the vertical component of the compression load caused by the filled carton immediately above a given carton, this compression load, in combination with the oxidative action of the bleach on the interior of the plastic bottle appears to accelerate or exacerbate cracking. Surprisingly, stress-cracking is substantially reduced when one of the above dispersing agents is used instead of common surfactants which cause wetting of the surface.

It is therefore an object of this invention to reduce or eliminate stress-cracking in an economical fashion in plastic bottles which contain fragranced bleaches and which bottles are packaged in cartons in which the bottles themselves directly share or bear part of the load caused by similarly-filled cartons which are stacked atop one another.

It is a further object of this invention to provide a chemical means for overcoming a mechanical problem arising in the packaging field.

It is another object of this invention to reduce or eliminate stress-cracking in plastic bottles irrespective of compression load thereon, said bottles containing liquid bleach with an additive immiscible to slightly miscible therein, which requires a dispersant to aid in dispersing said additive.

It is yet another object of this invention to provide a fragranced bleach composition which is substantially isotropic or one phase.

It is a still further object of this invention to provide a means for the improved manufacture of fragranced bleach compositions by providing a homogeneous fragrance preblend (and a method of making therefor) which is charged into a liquid bleach solution and yet substantially completely disperses within said liquid bleach.

DETAILED DESCRIPTION OF THE PREFERRED EMBODIMENT

Figure 1:
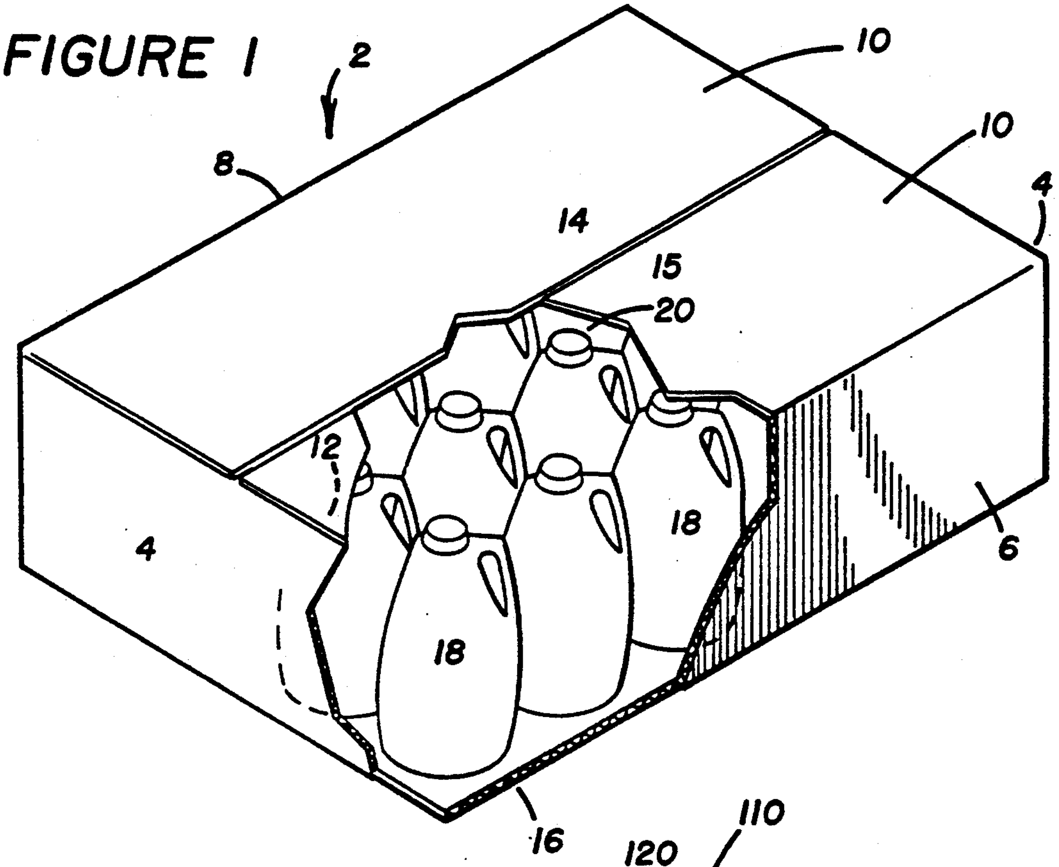
FIG. 1 shows one of the shipping containers of the invention, partially in section, in perspective.

The containing of liquid bleaches, whether hydrogen peroxide or hypochlorite-based, is typically provided in plastic vessels (jugs or bottles) in sizes varying from pint, quart and gallon-and-a-half, or other volumetric measure (e.g., metric). Such plastic bottles are made of relatively inexpensive materials, which are fairly tough and durable, easy to manufacture, and lightweight. For convenience of storage and shipping (whether by trucking, railcar or other means of drayage), the plastic vessels are loaded into corrugated shipping containers (also called cartons). These containers are typically stacked and palletized for ease of movement and storage Because storage space in warehouses and the like is at a premium, it is preferable to stack the containers very high. Stack loads of up to 12 or more containers or cases is typical. However, even though corrugated can be reinforced, such containers—which are typically formed from sheet material composition of paperboard combinations and cut out as blanks—can be crushed by heavy compression loads. For instance, if the containers bear heavy goods, such as filled plastic jugs, the weight of the uppermost containers can crush the corrugated containers on the bottom layers of the stack. Some manufacturers set tolerances for the corrugated containers and the plastic vessels contained therein such that there is substantially little or no clearance between the interior of the top panel of the corrugated and the top of the plastic vessels. In this manner, when corrugated containers are stacked, the plastic vessels themselves bear part of the load caused by such containers. This helps to minimize the total cost of the packaging system.

In the present invention, it was discovered that when fragranced bleaches are contained in the plastic vessels, and when surfactants are used to disperse insoluble adjuvants such as fragrances in the substantially aqueous bleach solution, stress-cracking in the plastic vessels increases when the bottles load-share.

Surprisingly, it was discovered that a certain class of dispersing materials, known as hydrotropes, or dispersing agents at a use concentration below that which causes wetting of the plastic, used in place of such surfactants, would substantially mitigate such stress-cracking.

Each of the components of the inventive shipping and storage system are described as follows.

1. Shipping Containers

The shipping containers (also called cartons or cases) used in the invention are typically made of single-wall corrugated board materials which are commonly used for shipping and storage containers of this type. Preferably, single-wall corrugated board having C flutes and a burst test strength of 200 p.s.i.g. are used. Different corrugated materials having different burst test strengths, e.g., 125, 175, or 275 p.s.i.g. can be used depending on strength and or cost requirements. Other materials, such as, fiberboard, pressed hard board, or other materials can be used and are known to those skilled in the art. It is not necessary that the containers be closed, i.e., that there be a bottom panel with 2 side and 2 end panels or walls dependent therefrom, which has a top panel closing the same (which top panel typically comprises extensions of the side and end panels). The containers could comprise trays such as those described in FIG. 1 (item 12) of Beeby, U.S. Pat. No. 3,348,667, or other construction known to those skilled in the art. The plastic vessels contained therein could be stabilized by plastic shrinkwrap or similar overwrap. In fact, viewing FIG. 3 of the present drawings, a single panel serving as the bottom panel could suffice as the container, although it is preferred that the panel have at least one wall dependent therefrom, and most preferable that the container have four walls.

2. Plastic Vessels

The plastic vessels, which can be bottles or jugs, are typically blow-molded plastics made of high density polyethylene (HDPE) and copolymers thereof. High density polyethylenes are particularly preferred for use in this invention. These types of polymers lend themselves very well to blow-molding and other manufacturing methods for making liquid-bearing bottles. These high density polyethylenes are manufactured by polymerizing ethylene under relatively low pressure in the presence of efficient catalysts, such as titanium halide-aluminum alkyl (Ziegler process) and chromium oxide promoted silica catalysts (Phillips process). There is also a new generation of HDPE's now available from DuPont/Nissei. These polymers have a density of about 0.940 $g/cm^3$ and greater, more preferably about 0.941–0.959 $g/cm^3$ for high density copolymers, and greater than, or equal to, 0.960 g/cm$^3$ for high density homopolymers. Typical homopolymers have a density of about 0.960–0.965 g/cm$^3$ yielding toughness and high shatter-resistance. It is most preferred to use copolymers with densities between 0.95 and 0.96. Conversely, while density is favored for rigidity and strength, it is sought to be reduced for increase in stress-cracking resistance and maintaining load bearing capacity. Molecular weight of the plastic should also be controlled to impart appropriate characteristics to the plastic. In these high density polyethylenes, density has an approximately inverse relation to molecular weight, as usually measured via melt index in units of g/10 min. As molecular weight increases, improvement in resistance to environmental stress cracking improves. Table I and II below relates these relationships (these tables are for illustration purposes only, since they are based on ASTM test methods that do not involve bleach; but they do indicate general trends for these grades of plastics):

TABLE I

Melt Index and Molecular Weight Relationship in Linear High Density Polyethylene[1]

| Melt Index g/10 min. | $M_w$[2] | ESCR[3] |
|---|---|---|
| 0.2 | 175,000 | 60 |
| 0.5 | 160,000 | |
| 1.0 | 140,000 | 14 |
| 5 | 90,000 | 1 |
| 10 | 75,000 | — |
| 20 | 60,000 | — |

[1]Adapted from "Olefin Polymers (Linear HDPL)", Kirk-Othmer Encyclopedia of Chemical Technology, 3rd Ed., Vol. 16, pp. 421–433 (1981), incorporated herein by reference.
[2]weight average molecular weight.
[3]Environmental stress crack resistance, Bell Test, number of hours to achieve 50% failures.

TABLE II

Density Dependent Properties of HDPE[a]

| Density, g/cm$^3$ | ESCR[b] |
|---|---|
| 0.94 | 700 |
| 0.95 | 100 |
| 0.96 | 20 |

[a]Adapted from 'Olefin Polymers (Linear HDPE)", Kirk-Othmer Encyclopedia of Chemical Technology, 3rd Ed., Vol. 16, pp. 421–33 (1981), incorporated herein by reference.
[b]Environmental Stress Crack Resistance, Bell test, number of hours to achieve 50 failures.

For blown bottles used to house liquid bleaches, a density of about 0.950–0.956 g/cm$^3$ and a melt index of about 0.1–0.5, most preferably 0.20–0.40, g/10 min. are preferred. In the invention, these particular parameters for these HDPE bottles are especially preferred since in a prior formulation for the liquid bleach composition containing a fragrance dispersed by a high wetting surfactant, higher amounts of a lower density plastic were used. By utilizing the present plastic, reduced costs result from greater manufacturing efficiency and less plastic per bottle.

Despite the impressive amount of knowledge that is known about high density polyethylene which is used to make blow-molded bottles and about designing appropriate parameters for bottles which contain liquid bleaches, in fact, when adjuvants are added which are slightly miscible to immiscible in such aqueous bleaches, the stress cracking such bottles can suffer when a vertical load is placed thereon can be greatly increased when an efficient dispersant or emulsifier, which "wets" the plastic, is added to the aqueous system. This problem has neither been heretofore recognized nor addressed in the prior art.

Blown HDPE bottles can have their properties modified by additives. For instance, it is preferred to modify the density of the polyethylene resin by co-polymerizing a small amount of a short chain alkylene, e g., butene, hexene or octene, with the ethylene. Various other additives could be added, such as colorants, opacifying agents, and antioxidants, such as hindered phenols, e.g., BHT, Irganox 1010 (Ciba-Geigy A.G.), Irganox 1076 (Ciba-Geigy A.G , Ionol (Shell Chemical Co.). Mold release agents and plasticizers could be added, especially to other types of plastics.

Other hydrocarbon polymers; polyvinyl chloride, suitably modified polystyrene, or copolymers thereof, might be considered for use, but are not as preferred because of cost and strength considerations. While certain materials, such as acrylonitrile, polyethylene terephthalate, polyethylene terephthalate glycol, polycarbonates and ABS (acrylonitrile butadiene styrene), polymers could be used, it is generally preferred to use cheaper plastics for ease of manufacture and to avoid high material costs. It is most preferred to use opaque or opacified plastics when they are used to make bottles for housing liquid bleach to prevent photodecomposition.

Suitable methods of forming and manufacturing the vessels of the invention are disclosed in *Kirk-Othmer. Encyclopedia of Chemical Technology,* 3rd Ed., Vol. 18, pp. 184–206 (1982), the disclosure of which is incorporated herein by reference.

It is particularly preferred that bottles of this invention be blow-molded. This is usually accomplished by, generally, providing a mold into which is introduced molten resin in the form of a parison. After the air is fed into the die, the parison expands to fill the mold and then is cooled to form the bottle. Thereafter, the bottle is removed from the mold.

Further, the bottles of the invention typically will have a relatively thin-walled construction, e.g., or 0.005–0.1 in., most preferably about 0.010 in. minimum. These vessels will typically have an appropriate interior volume ranging from one pint (16 fl. oz) to one and one half gallon (192 fl. oz). (Other volumetric measures e.g., metric, are possible). The bottles typically narrow into a depending finish and said finish is provided with a separate closure, which typically is screw-threaded and rotationally closes down on the finish which is usually provided with mating threads. Although not critical to the invention, the closure may be constructed of plastic which is generally different from the plastic used for the bottle, and typically is manufactured by different processing methods, e.g., injection molding. Lined metal closures are also common.

However, it is primarily the body of the plastic vessel or bottle which bears the compression load caused by the stacked cartons or cases. Although, to a significant extent, the liquid filling the volumetric extent of the bottle will act to hydraulically brace the relatively thin walls of the bottle, in fact, because of the highly reactive liquid medium, such plastic can be chemically attacked by such liquid. It is also to be emphasized that even when no compression load is placed on the bottles, a liquid bleach composition containing an additive dispersed by a strongly wetting surfactant can still attack the internal surface of the bottle to cause stress-cracking. The invention also substantially remedies this problem affecting free-standing bottles.

3. Liquid Oxidant Bleach

The preferred bleach stored in the plastic vessels of the invention is an alkali metal hypochlorite, most preferably sodium hypochlorite. The hypochlorite is typically about a 2–10%, preferably 5–6%, solution of sodium hypochlorite in water, with various amounts of sodium hydroxide, sodium chloride and other by-products of the manufacturing process present. Small amounts of buffer, e.g., sodium carbonate, are typically added. Hypochlorites are, of course, very effective oxidants and useful in a wide variety of cleaning and laundering applications.

4. Fragrances

Fragrances are usually blends of volatile oils that are composed of organic compounds such as esters, aldehydes, ketones or mixtures thereof. Such fragrances are usually proprietary materials commercially available from such manufacturers as Quest, International Flavors and Fragrances, Givaudan and Firmenich, Inc. Examples of fragrances which may be suitable for use in the present invention may be found in Laufer et al, U.S. Pat. No. 3,876,551, and Boden et al, U.S. Pat. No. 4,390,448, the specifications of both of which are incorporated herein by reference.

Fragrances, however, are typically not totally miscible in aqueous solution. Because of their low miscibility in such aqueous solutions, including bleach solutions, there is the danger that such fragrances will pool and form a separate phase from the aqueous portion of the liquid. This will be disadvantageous. Fragrances will not be dispensed evenly since the bleach is dispersed in small "use" amounts each time (e.g., one cup) and only very small amounts of fragrance will be dispersed in most uses. Thus, the benefit intended—fragrancing—is not available. On the other hand, because of the uneven fragrancing some use dosages may contain too much fragrance, thus leading to overperfuming a laundry load. Additionally, it is not as esthetically pleasing to have a separated, two phase liquid system as it is to have a one phase, relatively isotropic system.

Thus, the need to have a single phase system led to the use of dispersing materials to disperse these immiscible materials in the aqueous, continuous phase of the liquid system. Thus, in numerous prior references, materials such as surfactants in amounts sufficient to wet the plastic bottles were used to disperse fragrances. In Laufer et al, amine oxides were used as the sole dispersing material for fragrances in a liquid hypochlorite bleach. Boden et al, U.S. Pat. No. 4,390,448, disclose the use of a diphenyl oxide disulfonate as a dispersant for a fragrance. However, it was found that the use of a surfactant-type material in a sufficient amount to disperse the fragrance led to the accelerated stress-cracking observed in the plastic vessels when such vessels were placed under a load as in the stacked containers. It is not exactly understood why this phenomenon is so. But it has been observed that the interior of the plastic bottle was wetted more in the presence of the surfactant. Surfactants are dispersing materials which typically have a hydrophobic portion consisting of at least one long chain alkyl, and a water miscible or soluble portion which may be charged (e.g., zwitterionic (e.g., betaine), cationic (e.g., quaternary ammonium) or anionic (e.g.s., sulfonate or carboxylate)) or uncharged (e.g.s., ethoxylated or propoxylated alcohols). Common to these surfactants is the ability to form micelles, in which the molecules of the surfactants orient themselves in an aqueous medium, to have the hydrophobic portion localized in the interior of the micelle and the charged or hydrophilic portions oriented to the exterior of the micelle. However, it is these surfactant materials which appear to promote stress-cracking in the plastic vessels when used as the dispersants for immiscible fragranced materials in liquid oxidant bleaches. The key consideration appears to be that the use of surfactants increases wetting of the plastic surface. Surfactants present in high enough concentration so lower surface tension of bleach below the critical surface tension of the bottle such as to cause wetting of the plastic. It is believed such wetting accelerates or increases reaction of the oxidant bleach and the bottle.

If other immiscible, to slightly miscible adjuvants are desirable, they can be selected from dyes, fluorescent whitening agents (FWA's), pigments, opacifying agents, solvents, and the like. See, e.g. U.S. patent application Ser. No. 06/831,774, Kaufmann et al, filed Feb. 20, 1986, pages 21–22 of which are incorporated herein by reference.

5. Non-wetting dispersing agents

Many preferred agents are classified as hydrotropes. Hydrotropes are generally described as non-micelle-forming substances, either liquid or solids, organic or inorganic, which are capable of solubilizing insoluble compounds in a liquid medium. The classical definition was first considered by Neuberg, *Biochem. Zeit.* Vol. 76, pp. 107–176 (1916) (which pages are incorporated herein by reference). As with surfactants, it appears that hydrotropes must interact or associate with both hydrophobic and hydrophilic media. Cf.. Lawrence et al, "Solubilization and Hydrotropicity," in: *Chemistry, Physics and Application of Surface Active Substances,* Vol. II, pp. 673–708 (1964). See also, Rath, "The Nature of Hydrotropicity and its Significance for the Chemical Technology," (translation), *Tensile,* Vol I, pp. 1–6 (1965) (both of which are incorporated herein by reference). Unlike surfactants, typical hydrotropes do not appear to readily form micelles in aqueous media on their own. In the present invention, it is crucial that the hydrotrope act as a dispersant, but that it does not decrease the surface tension below the critical surface tension of the plastic substrate. "Critical surface tension" is defined in W. A. Zisman, "Relation of the Equilibrium Contact Angle to Liquid and Solid Constitution," *Adv. Chem. Series,* Vol. 1, pp. 1–51 (1964), the disclosure of which is incorporated herein by reference. Critical surface tension defines the maximum value in dynes/cm of the surface tension of a liquid, below which the plastic substrate can be wetted. By "wetting", the ordinary lay definition of a solid substrate merely covered by liquid is not meant. Instead, wetting is defined as when the liquid will spontaneously spread over the surface instead of forming droplets. This can be observed by seeing whether a liquid beads up (non-wetting) or runs over (wetting) the surface of a planar substrate. Critical surface tension is explained by Young's equation, which is $$\gamma_{L/A} \cos\theta = \gamma_{S/A} - \gamma_{S/L}.$$

In a pragmatic sense, if a material acts to disperse an immiscible solute, i.e., fragrance, in an aqueous medium without causing the plastic substrate to be physically "wetted", such that large masses of aqueous liquid remain adhered to the plastic substrate, such material is hydrotropic. Another, more pragmatic way of determining wetting is to measure the contact angle of a droplet of liquid on the solid substrate. Contact angle is the actual measurement of the tangent of the liquid droplet at the point of contact with respect to the planar surface on which it rests. Measurements can be conducted via a goniometer or other devices. The lower the contact angle, the more strongly the liquid is wetting. In Table III below, critical surface tension in dynes/cm for representative plastics is set forth. In Table IV, the "wetting" of polyethylene via various dispersant materials is set forth.

TABLE III

Critical Surface Tension of Plastics[1]

| Polymer | Critical Surface Tension dynes/cm |
|---|---|
| poly(vinylidene chloride) | 40 |
| poly(vinyl chloride) | 39 |
| polyethylene | 31 |
| poly(vinyl fluoride) | 28 |
| poly(vinylidene fluoride) | 25 |
| polytrifluoroethylene | 22 |
| polytetrafluoroethylene (Teflon) | 18 |

[1]Adapted from W. A. Zisman et al, "Relation of the Equilibrium Contact Angle to Liquid and Solid Constitution," pp. 1-51, in Contact Angle: Wetability and Adhesion, Advances in Chemistry Series, 43 (1964).

TABLE IV

Effect of Dispersant on HDPE[1]

| Material | Dispersant | Contact[5] Angle,° | Surface[6] Tension dynes/cm |
|---|---|---|---|
| 1. Distilled Water | none | 88 ± 3 | 73 ± 2 |
| 2. Hypochlorite Bleach[2], 5.25% | none | 87 ± 3 | 52 ± 2 |
| 3. Hypochlorite Bleach[2], 5.25% Velvetex AB45[4] | 0.08% Stepanate X[3] with 1.1 ppm | 88 ± 3 | 34 ± 2 |
| 4. Hypochlorite Bleach[2], 5.25% | 0.02% Velvetex AB45[4] | 50 ± 3 | 27 ± 2 |

[1]High density polyethylene, 0.940-0.965 g/cm$^3$.
[2]Regular strength commercial bleach.
[3]Sodium xylene sulfonate from Stepan Chemicals (41% Active).
[4]Dimethyl Cocobetaine from Henkel KGaA (36.5% active).
[5]These runs were made with new polyethylene and freshly made solutions.
[6]This is the liquid/air surface tension.

The data in TABLES III and IV demonstrate that the surface tension of the liquid/air interface is very important to determining wetting of the plastic substrate. If the surface tension of the solutions depicted in TABLE IV are above the critical surface tension of polyethylene, then no wetting should occur. This was confirmed by the contact angle measurements.

As can be seen above, surfactant in an amount sufficient to disperse a fragrance will cause wetting of the plastic. Similarly, it should be noted that concentration or amount of the material, as well as type, may also be critical towards determining whether such material is a hydrotrope. Thus, materials which ordinarily are classified surfactants may in fact behave as hydrotropes if the amount used is limited. The high ionic strength of many bleach solutions often causes surfactants to reduce surface tension greater than in accordance with published values. Thus, the threshold concentration for some surfactants where they begin to cause wetting can be very low. In certain instances, these concentrations can be so low that sufficient dispersion does not occur. In such instances, an additional hydrotrope would be needed. In the invention, the amount of hydrotrope used can be quite low—from about 10 ppm to 100,000 ppm, or about 0.001% to 10%, more preferably 0.01 to 1%. Higher amounts may also be suitable provided wetting of the plastic substrate is not achieved, but is less preferred as they add higher materials costs.

The preferred hydrotropes appear to be alkali metal salts of benzoic acid and its derivatives; alkyl sulfates and sulfonates with 6-10 carbons in the alkyl chain, $C_{8-14}$ dicarboxylic acids, anionic polymers such as polyacrylic acid and their derivatives; and most preferably, unsubstituted and substituted, especially the alkali metal salts of, aryl sulfonates; and unsubstituted and substituted aryl carboxylates. As used herein, aryl includes benzene, napthalene, xylene, cumene and similar aromatic nuclei. Further, "substituted" aryl means that one or more substituents known to those skilled in the art, e.g., halo (chloro, bromo, iodo, fluoro), nitro, or $C_{1-4}$ alkyl or alkoxy, can be present on the aromatic ring. Other good dispersants include other derivatives of aryl sulfonates, salts of phthalic acid and its derivatives and certain phosphate esters. Most preferred are alkyl naphthalene sulfonates (such as Petro 22 available from Petro Chemicals Company) and sodium xylene sulfonate (such as Stepanate X, available from Stepan Chemical Company.

SURFACTANTS

As just discussed, when surfactants are used as the dispersants for fragrance in liquid bleach which will be housed in plastic bottles, stress-cracking is exacerbated, especially under load share conditions. However, it has also been found that when a minimal amount of a surfactant is used, dispersion of the fragrance or other immiscible to slightly miscible adjuvant may be substantially enhanced. In particular, as discussed in greater detail herein below, use of such minimal amounts of surfactants aids in the manufacture of homogeneous fragrance preblends. In the finished bleach product, it is preferred that 0-100 ppm, most preferably 0.5-20 ppm, of said surfactant, is present. Appropriate surfactants are dimethyl alkylbetaines (e.g., dimethyl cocobetaines, Velvetex AB 45, from Henkel KGaA), trialkyl amine oxides (dimethyl, dodecyl amine oxide, such as Barlox 12, from Lonza Chemical), trimethyl, alkyl quaternary ammonium compounds, secondary alkane sulfonates (AKA paraffin sulfonates, and the like. e.g., DeSimone, U.S. Pat. No. 4,113,645, Nayar et al, U.S. Pat. No. 4,623,476, Diamond et al, U.S. Pat. No. 4,388,204, Stoddart, U.S. Pat. No. 4,576,728, Bentham et al, U.S. Pat. No. 4,399,050, Schilp, U.S. Pat. No. 4,337,163, and Choy et al, U.S. Pat. Nos. 4,657,692 and 4,599,186, all of which are incorporated by reference and give ample exemplification of appropriate surfactants.

DETAILED DESCRIPTION OF THE DRAWINGS

Referring now to the drawings, FIG. 1 generally depicts a corrugated container 2, which is representative of one of the containers forming the units in the storage and shipping system of the invention. The container 2 is generally constructed by taking a corrugated blank and subjecting it to a die or other means of forming perforations, slits or the like in such blank, and then folding, and fastening the panels together with glue, staples or other means, in order to prepare such containers. In the present invention, the container 2 has a bottom 16 from which depend side panels 6, 8 and end panels 4, 4. The top 10 generally comprises side flaps 14, 15. Side flap 14 is an extension of side panel 8. Side flap 15 is an extension of side panel 6. Partially shown end flap 12 is an extension of side 14. Housed inside the container 2 are a plurality of bottles 18 which are fitted with closures 20. These bottles will house the fragranced bleach. The bottles are constructed of a high density polyethylene with melt index of about 0.22–0.35 and a density of about 0.950–0.956 g/cm$^3$. The fragranced bleach contains about 5–6% sodium hypochlorite, 0.001–1% fragrance, 0.0001–1% sodium xylene sulfonate and about 0.5–20 ppm cocobetaine surfactant, and the remainder, water.

Figure 2:
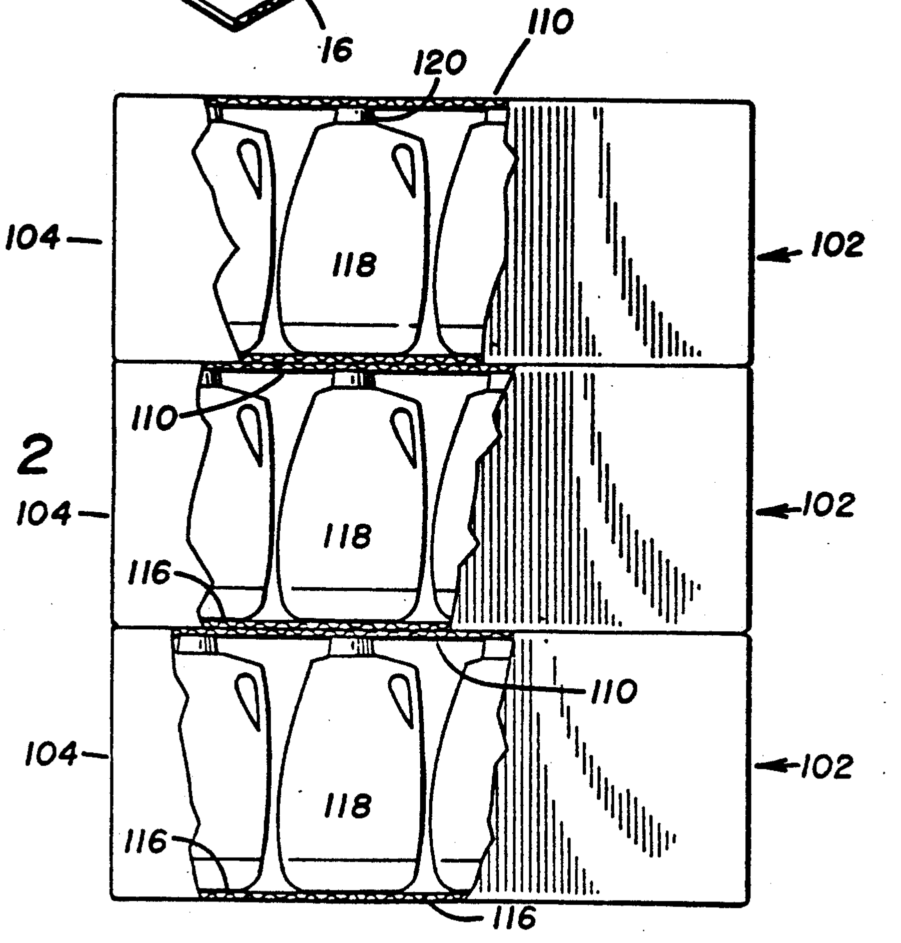
FIG. 2 shows a side elevational view of a partial stack comprising three of the inventive storage and shipping containers, with a cutaway view of the interior of the containers.

In FIG. 2, a side elevational view of three stacked containers is depicted. In this side elevational view, containers 102 are shown partially in section. Side panels 106 are partially cut away to reveal the interior. As can be seen, the bottles 118 fitted with closures 120 are carried within such containers 102. The bottles 118 are fitted in the interior of containers 102 such that there is virtually no clearance or space between the top of closure 120 and the top panel 110. Thus, in an given arrayed stack, the compression load provided by the stacked containers will be directly translated from the carton and its bottom panel 116 to the container 102 directly below through top panel 110, and thence to closure 120 and the body of bottle 118.

Figure 3:
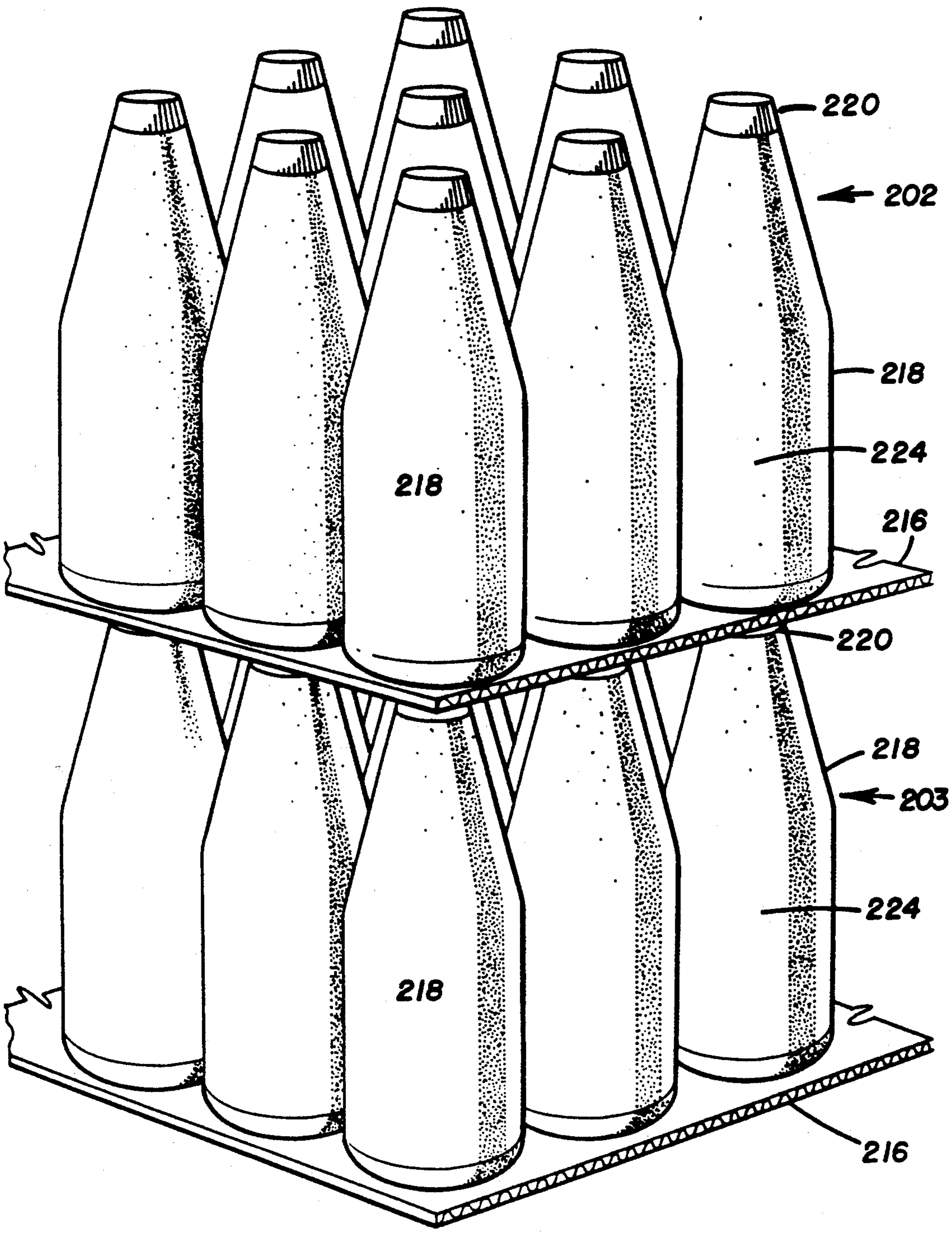
FIG. 3 is a perspective view showing only a row of plastic bottles, the top layer of which rest on a bottom panel of a carton, which rest directly on the top of the row immediately below it.

In FIG. 3, a perspective view of a further embodiment of the shipping and storage system is disclosed in which containers 202, 203 are again stacked. However, only panel 216 is used as a stacking and separating means for containers 202 and 203, which each comprise merely rows of bottles 218. Bottles 218 with closures 220 rest upon panel 216. Again, there is little or no clearance between panel 216 of the container 202 and the closures 220 of the bottles 218 of container 203. Thus, the compression load is directly translated to the bodies 224 of bottles 218.

In the Experimental section which follows below, various compression tests were conducted in which plastic bottles or the materials used to make such plastic bottles were placed under various weight loads to show the impact of mechanical forces on such materials. However, in order to assess the additional chemical stresses that are placed on such bottles, the bottles included the preferred fragranced bleach formulations. A comparison was made with formulations in which the dispersant used for the fragrance was a "wetting amount" of a surfactant. As a control, an unfragranced bleach was tested.

EXPERIMENTAL

1. Bottled Topload Stress Crack Test (120° F.)

In the bottle topload stress crack test, the stress crack resistance of blow-molded plastic bottles under a static topload is compared to a known standard (that is, a control). The topload test measures a bottle's resistance to environmental stress cracking while under a mechanical (toploading) and chemical (product) stress. To prevent unrealistic mechanical stress, bottle deflection is to be less than or equal to the bottle's yield point. Bottle deflection is here defined as the measurement in distance units corresponding to the distance the device placing a weight or mechanical force on the bottle is displaced. The yield point is the maximum deflection a bottle can tolerate before either losing compression strength, permanently creasing, or changing its original shape.

The device used in the bottle topload stress crack test is a topload bench assembly, which consists of a platform which is hydraulically or mechanically loaded atop the laboratory bench and which is raised or lowered by means of a crank. The platform is provided with individual deflection contacts which are fitted over the bottles to be tested. The deflection is measured out in mm. or in. Separately the vertical load or compression can be measured in force units (pounds or Newtons). By reference to standards which have been separately developed, the amount of deflection used on control is used as a comparison for new products.

The tests are conducted at 120° F. The product to be used is 5.25% (with ±0.25%) liquid hypochlorite bleach. The bottles filled with product are conditioned at room temperature for 12–24 hours. The bottles are then closed with suitable closures to ensure an air-tight seal. The bottles are then allowed to equilibrate for 3–6 hours at 120° F. to allow internal pressure to build up. Thereafter, the conditioned bottles are placed under the displacement platform and placed under stress. At this point, the deflection platform is lowered onto the bottles and cranked down 1/16" every two hours until the maximum deflection listed in the independently generated bottle standard is reached. After 24 hours, the bottles are checked for failures. Failures would be noted by loss of internal pressure from locations other than the bottle/closure seal, or if there is evidence of product on the bottle exterior coming from an opening other than the bottle/closure seal.

2. Tensile Bar Test

Yet another method for assaying environmental stress cracking at elevated temperatures is the tensile bar test. In this test, the plastic material used to make the bottle is used as a model to simulate what would happen if the bottle were subjected to the same environmental stresses. The plastic materials are injection-molded plastic bars. Typically, flat plates or bars of about 1 and ¼" width by 4" length which have somewhat square-shaped arms which have 1 ¼" width and 1" length. A 0.5 mm notch is cut into the narrow part prior to testing, which allows crack propagation along a given path. These bars are immersed in the liquid product during the test in order to simulate the same conditions occurring as in the bottle topload stress test. In order to test these bars then, the bars are held by T-shaped clamps which are mounted on a lever arm suspended from an elevated platform. In order to provide a mechanical force to the bars, weights in the form of lead shot or other appropriate materials are loaded in containers which are then hung on the lever arm opposite the clamps. Thereafter, a glass cylinder or other, similar container is filled with the liquid bleach product and such cylinder is fitted under the mounted arm to complete the simulation of a stacked load. The bars are then tested in a 120° F. environment room or the cylinders containing the product are immersed in a 120° F. water bath. Stress cracking is then monitored by measuring crack lengths in the bars daily for ten days.

Using the above test, plastic bars were made by injection molding a commonly used polyethylene material (Soltex B54-25H-96 manufactured by Soltex). This bar was immersed in four cylinders for each of three different products: (A) a fragranced liquid bleach using a dimethylcocobetaine as a dispersant for a fragrance; (B) a control material containing neither fragrance nor dispersant; and (C) a formulation containing the inventive composition with a fragrance and sodium xylene sulfonate as the fragrance dispersant. The formulations are disclosed below:

TABLE V

| | A Bleach Containing Surfactant as Fragrance Dispersant | B Control (No Fragrance No Dispersant) | C Bleach Containing Hydrotrope as Fragrance Dispersant |
|---|---|---|---|
| NaOCl | 5.25% | 5.25% | 5.25% |
| Fragrance (immiscible) | 0.02% | — | 0.02% |
| Dispersant: | | | |
| Velvetex AB-45[1] | 0.02% | — | — |
| Stepanate X[2] | — | — | 0.08% |
| NaOH | minor | minor | minor |
| NaCl | 4.0% | 4.0% | 4.0% |
| $Na_2CO_3$ | minor | minor | minor |
| Water | Q.S. | Q.S. | Q.S. |
| | 100.00% | 100.00% | 100.00% |

[1]36.5% dimethylcocobetaine from Henkel KGaA.
[2]41% sodium xylene sulfonate from Stepan Chemicals.

The results for the tensile bar test for the above product were as follows:

TABLE VI

| Product | Average crack length in mm (over 10 day period) |
|---|---|
| A | 6.2 |
| B | 1.2 |
| C | 1.3 |

The results show that use of hydrotrope as a dispersant for the fragranced bleach surprisingly does not increase stress-cracking as against control in an experiment simulating the compression load placed on plastic bottles used to contain fragranced bleaches when cartons carrying such bottles are stacked In Table VII below, dispersant levels are determined by visual grading in accordance with the polyethylene wetting test. In such test, on a scale of 1 to 5 (1=grade hypochlorite bleach, i.e., no wetting; 5=hypochlorite with fragrance completely dispersed by a high amount of a high wetting surfactant), the wetting capability of the dispersants is ascertained:

DISPERSION AND WETTING RESULTS

| EXAMPLE | COMPOUND | CRITICAL DISPERSANT LEVEL[1] % | CRITICAL DISPERSANT LEVEL[1] mM | TESTED LEVEL % | TESTED LEVEL mM | POLY-ETHYLENE WETTING GRADE (1 TO 5)[2] |
|---|---|---|---|---|---|---|
| 1 | Dimethyl Cocobetaine, Na Salt | 0.0072 | 0.027 | 0.0090 | 0.033 | 5 |
| 2 | Amine Oxide, Lauryl Dimethyl | 0.0060 | 0.026 | 0.0060 | 0.026 | 4 |
| 3 | Amine Oxide, Myristyl Dimethyl | 0.0060 | 0.024 | 0.0060 | 0.024 | 5 |
| 4 | Dodecyl Diphenyl Oxide Disulfonate, Na Salt | 0.0081 | 0.015 | 0.0081 | 0.015 | 5+ |
| 5 | Hexyl Diphenyl Oxide Disulfonate, Na Salt | 0.014 | 0.030 | 0.014 | 0.030 | 4 |
| 6 | Octyl Phosphate Ester, Na-Salt | * | * | 0.047 | 0.14 | 5 |
| 7 | Butyl Phosphate Ester, Na Salt | * | * | 0.10 | 0.34 | 3 |
| 8 | Toluene Sulfonate, Na Salt | * | * | 0.095 | 0.49 | 1 |
| 9 | Xylene Sulfonate, Na Salt | * | * | 0.041 | 0.20 | 1 |
| 10 | Cumene Sulfonate, Na Salt | * | * | 0.19 | 0.86 | 3 |
| 11 | Benzene Sulfonate, Na Salt | * | * | 0.20 | 1.11 | 2 |
| 12 | Methylnaph-thalene Sulfonate, Na Salt | * | * | 0.038 | 0.16 | 3 |
| 13 | Octyl-Capric Acid, Na Salt | * | * | 0.066 | 0.37 | 5+ |
| 14 | Capric Acid, Na Salt | * | * | 0.066 | 0.34 | 5+ |
| 15 | Octane-Dicarboxylic Acid, Na Salt | * | * | 0.10 | 0.41 | 2 |
| 16 | Octyl Sulfonate Na Salt | * | * | 0.018 | 0.083 | 1− |
| 17 | Octyl-Decyl Sulfate, Na Salt | 0.011 | 0.045 | 0.011 | 0.045 | 5 |
| 18 | T-Butyl Alcohol | 0.11 | 1.49 | 0.11 | 1.49 | 4 |
| 19 | Cetyl Trimethyl Ammonium Chloride | 0.0029 | 0.0091 | 0.0029 | 0.0091 | 5 |

-continued

| | | DISPERSION AND WETTING RESULTS | | | | |
|---|---|---|---|---|---|---|
| | | CRITICAL DISPERSANT LEVEL[1] | | TESTED LEVEL | | POLY-ETHYLENE WETTING GRADE |
| EXAMPLE | COMPOUND | % | mM | % | mM | (1 TO 5)[2] |
| 20 | Dodecyl Trimethyl Ammonium Laurate | 0.016 | 0.037 | 0.016 | 0.037 | 5 |
| 21 | Benzoic Acid, Na Salt | * | * | 0.20 | 1.39 | 4 |
| 22 | Salicylic Acid, Na salt | * | * | 0.20 | 1.25 | 4 |

[1]Level at which 0.02% fragrance is completely dispersed.
[2]Grade 1 = hypochlorite bleach, 5.25% (low wetting; no fragrance or surfactant); grade 5 = hypochlorite bleach with completely dispersed fragrance (mediated via surfactant), commercially sold as Fresh Scent Clorox ® Bleach, e.g. 1 (high wetting).
* Complete dispersion never achieved; droplet size less than 1 mm at level tested.

The data in Table VII demonstrate that for best fragrance dispersion and minimized wetting on a polyethylene surface, an averaged grade of no greater than 4, more preferably no greater than 3.5, and most preferably, no greater than 3 is desirable. These tests were conducted on new polyethylene bottle.

METHOD OF MAKING PREBLEND

In a further embodiment of this invention a homogeneously dispersed fragrance preblend is provided. It should be understood that a preblend is, however, merely one manner of providing a liquid bleach with an appropriate dosage of fragrance. There are other ways of accomplishing this known to those skilled in the art. However, in the invention, providing the preblend is especially advantageous. As previously discussed, it is difficult to disperse fragrance evenly in an aqueous solution, such as liquid hypochlorite bleach. In the preferred method of the invention, a preblend comprising a homogeneous mixture of fragrance, dispersant (hydrotrope), water and a minimal amount of a surfactant is provided. The preblend can be dosed into a liquid bleach in volume, or, preferably, by being automatically metered into each bottle in a line assembly. Examples of apparently appropriate metering devices are Meshberg, U.S. Pat. No. 4,061,247, and Botkin, U.S. Pat. No. 4,172,539, both of which are incorporated herein by reference. A homogeneous preblend is critical for even distribution of the fragrance to the liquid bleach. If not homogeneous, when the preblend is automatically dosed or metered into the liquid bleach, uneven amounts of fragrance could result for different batches of product, leading to quality control problems. Mechanical emulsification of the preblend could be a partial solution to this problem. However, such a step would then add further manufacturing and equipment costs, and would be much less efficient than the method of the invention.

The fragrance preblend is a mixture of components in the ranges of 0.5–15% (preferably 1–6%) fragrance; 1–25% (preferably 5–20%) hydrotrope; 0.001–0.09% (preferably 0.005–0.05%) surfactant; and 60–98% water and miscellaneous.

By adding a minimal amount of surfactant, the stability of the preblend (which is actually an emulsion of water, hydrotrope and fragrance oil) is dramatically improved. The method of preparing is as follows: A preferred order of addition (although other orders of addition are also possible) is to charge, sequentially, water, minimal amounts of surfactant, hydrotrope and fragrance oil into a large vessel which is typically a vat provided with an impeller which is constantly agitating at an angular velocity of 10–500 rpm, and for a period of at least 5 minutes, more preferably at least 10 minutes, and most preferably, under constant agitation so as to form a milky white, emulsion. A example of the practice of this method follows. A 450 lb preblend was prepared by:

| Preblend Preparation | |
|---|---|
| Ingredients | Wt % |
| Water | 78.477 |
| Sodium Xylene Sulfonate[1] | 17.2 |
| Dimethyl Cocobetaine[2] | 0.023 |
| Fragrance[3] | 4.3 |

[1]Hydrotrope, available as a 41% active solution (thus, actual Wt. % = 7.052%).
[2]Bleach stable surfactant, available as about 36.5% active solution (thus, actual Wt. % = 0.0084%).
[3]Available from Quest.

In the order listed, each ingredient was separately charged into a 55 gallon mixing drum and agitated. A metering doser was affixed in-line to meter dosages of the fragrance preblend into a hypochlorite bleach so as to provide a fragranced bleach product with the following final formulation:

| Ingredient | Wt % |
|---|---|
| NaOCl | 5.25 |
| Sodium Xylene Sulfonate | 0.0328 |
| Fragrance | 0.02 |
| Dimethyl Cocobetaine | 0.0000391 |
| Water, NaOH, NaCl, $Na_2CO_3$, miscellaneous | Q.S. |
| | 100.0000000% |

PREBLEND STABILITY TEST

Various combinations of fragrance, hydrotrope, surfactant, and water in prototype fragrance preblends were made up to test for physical stability. In this procedure, 3 liter batches were made in the preferred order of addition, mixed in a 4 liter beaker equipped with a magnetic stir bar. The samples were mixed at high angular velocity ~300 rpm) for 10 minutes. The particular surfactant used, Velvetex AB (Henkel KGaA, 36.5% active dimethyl cocobetaine) was weighed out on an analytical balance. After mixing 10 minutes, 50 ml burettes were filled with the mixture. Criterion for acceptable stability was less than 0.5 ml separation within 15 minutes. (Fragrance from Quest was constant at 4.3 wt. % in the batches).

TABLE VIII

Preblend Stability

| Example | % Water | % hydrotrope[1] | % Surfactant[2] | Time (Min) to 0.5 ml Separation |
|---|---|---|---|---|
| 1 | 95.6570 | 0.0 | 0.043 | 10.5 |
| 2 | 85.6880 | 9.9880 | 0.024 | 15.0[3] |
| 3 | 85.6880 | 9.9880 | 0.024 | 15.0[3] |
| 4 | 95.6760 | 0.0 | 0.024 | 8.0 |
| 5 | 95.6950 | 0.0 | 0.005 | 6.0 |
| 6 | 85.6975 | 9.9975 | 0.005 | 15.0 |
| 7 | 85.6880 | 9.9880 | 0.024 | 15.0[3] |
| 8 | 85.6785 | 9.9785 | 0.043 | 15.0[3] |
| 9 | 75.7000 | 19.9950 | 0.005 | 11.0 |
| 10 | 75.7000 | 19.9570 | 0.043 | 15.0 |
| 11 | 75.7000 | 19.9760 | 0.024 | 14.0 |

[1]Stepanate X (41% active sodium xylene sulfonate, Stepan Chemical Co.).
[2]Velvetex AB (36.5% active dimethyl cocobetaine, Henkel KGaA).
[3]No separation observed.

Based on the foregoing test, addition Of about 0.010–0.05% surfactant provided surprisingly improved stability. This was especially surprising when compared to a prior art preblend which had no hydrotrope and about 4.3% (1.57% active) surfactant (as the sole dispersant) which had similar stability, but also, as discussed previously, led to a bleach formulation which increased stress-cracking in high density polyethylene bottles.

In the foregoing discussion of the inventive method and preblend, surfactants, hydrotropes and fragrances previously defined in this application are suitable for use in the method and in the preblend, with the additional proviso that if the preblend were used for a non-bleach-containing liquid, any surfactant could be used in the small amounts necessary for good dispersion The invention is further defined without limitation of scope or equivalents by the claims which follow.

We claim:

1. A homogeneous, bleach-stable fragrance preblend used to fragrance liquid hypochloride consisting essentially of:

(a) about 0.15–15% fragrance (b) about 1–25% hydrotrope (c) about 0.001–0.09 surfactant; and (d) water and miscellaneous minors as the remainder.

2. The fragrance preblend of claim 1 wherein said surfactant is in an amount sufficient to provide physical stability of the preblend such that after 15 minutes from preparation, there is less than 0.5 ml separation of a 50 ml sample of said preblend.

3. The fragrance preblend of claim 1 wherein said hydrotrope is selected from the group consisting of: unsubstituted and substituted aryl sulfonates, unsubstituted and substituted aryl carboxylates, $C_{6-10}$ alkyl sulfonates, $C_{8-14}$ alkyl dicarboxylates and mixtures thereof.

4. A method of making a homogeneous, bleach-stable fragrance preblend suitable to fragrance a liquid hypochlorite bleach, said method consisting essentially of; mixing, for at least 5 minutes, in order, (a) about 60–98% water;

(b) about 0.001–0.09% surfactant;

(c) about 1–25% hydrotrope; and (d) about 0.15–15% fragrance.

5. The method of claim 4 wherein said hydrotrope is selected from the group consisting of: unsubstituted and substituted aryl sulfonates, unsubstituted aryl carboxylates, $C_{6-10}$ alkyl sulfonates, $C_{8-14}$ alyl dicarboxylates and mixture thereof.

* * * * *